United States Patent [19]

Merger et al.

[11] Patent Number: 4,459,236

[45] Date of Patent: Jul. 10, 1984

[54] PREPARATION OF 1-ALKENYL ISOCYANATES

[75] Inventors: Franz Merger, Frankenthal; Hans-Martin Hutmacher, Mannheim; Friedrich Towae, Ludwigshafen, all of Fed. Rep. of Germany

[73] Assignee: BASF Aktiengesellschaft, Fed. Rep. of Germany

[21] Appl. No.: 329,126

[22] Filed: Dec. 9, 1981

[30] Foreign Application Priority Data

Dec. 31, 1980 [DE] Fed. Rep. of Germany ....... 3049627

[51] Int. Cl.$^3$ .................. C07C 125/06; C07C 118/04
[52] U.S. Cl. ................... 260/453 P; 560/24; 560/25
[58] Field of Search ............... 260/453 P; 560/24, 25

[56] References Cited

U.S. PATENT DOCUMENTS 3,992,430 11/1976 Bacskai ........................... 260/453 P

FOREIGN PATENT DOCUMENTS

| 1922412 | 5/1969 | Fed. Rep. of Germany ... 260/453 P |
| 2512514 | 3/1975 | Fed. Rep. of Germany ... 260/453 P |
| 2756928 | 12/1977 | Fed. Rep. of Germany ... 260/453 P |

OTHER PUBLICATIONS

Guia, et al., Chem. Abstracts, vol. 24, p. 3212, (1930).
Ullmanns Encyklopädie der Technischen Chemie, vol. 17, p. 204, (3rd Edition).
Houben–Weyl der Organischen Chemie, vol. 8, (1952), pp. 126–128.
J. Org. Chem. 26, (1961), pp. 770–779.
Chem. High Polymers (Tokyo) 13, (1956), p. 390.
J. Polym. Sci. 35, (1959), pp. 215–218.
J. Coatings Techn. 49, (1977), pp. 82–86.
Ullmanns Encyklopädie der Technischen Chemie, vol. 9, pp. 11, 12 and 404.

*Primary Examiner*—Henry R. Jiles
*Assistant Examiner*—Robert C. Whittenbaugh
*Attorney, Agent, or Firm*—Keil & Weinkauf

[57] ABSTRACT

1-Alkenyl isocyanates are prepared by reacting aldehydes with carbamates to give N-(1-alkenyl)-carbamates and splitting these compounds at elevated temperatures. The 1,2-unsaturated isocyanates obtained are valuable starting materials for the preparation of pest control agents, dyes, drugs, textile water repellents, detergents, plastics, bleaches and adhesives, since they possess an activated double bond or an activated α-carbon atom, in addition to a reactive isocyanate group.

8 Claims, No Drawings

PREPARATION OF 1-ALKENYL ISOCYANATES

The present invention relates to a process for the preparation of 1-alkenyl isocyanates by reacting aldehydes with carbamates to give N-(1-alkenyl)-carbamates and splitting these compounds at elevated temperatures.

The preparation of isocyanates by thermal decomposition of ureas and carbamates has been disclosed (Houben-Weyl, Methoden der Organischen Chemie, Volume 8, pages 126–128 (1952)). However, splitting of carbamates containing unsaturated substituents on the nitrogen to give N-alkenyl isocyanates has not been disclosed. The decomposition of naphthyl carbamates is proposed in German Laid-Open Application DOS No. 2,512,514, and the splitting of aryl carbamates in the liquid phase is proposed in German Laid-Open Application DOS No. 2,756,928. Both processes use starting materials which can be economically prepared only by phosgenation reactions. No examples of splitting to give 1-alkenyl isocyanates are given.

The preparation of 1-alkenyl isocyanates by catalytic decomposition of N-tert.-alkyl-N-(1-alkenyl)-carbamyl chlorides (German Published Application DAS No. 1,922,412) requires intermediates which must be prepared using phosgene. It has also been disclosed that 1-alkenyl isocyanates can be prepared by Curtius degradation of azides (J. Org. Chem., 26 (1961), 770–779). This synthesis route is unfavorable, not only because of the high cost of starting materials, but also, in particular, for safety reasons.

We have found that 1-alkenyl isocyanates of the formula

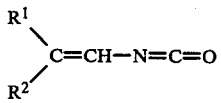

where $R^1$ and $R^2$ can be identical or different and each is hydrogen, halogen or an aliphatic, cycloaliphatic, araliphatic or aromatic radical, or $R^1$ and $R^2$, together with the adjacent carbon, are members of a ring, are obtained in an advantageous manner when an aldehyde of the formula

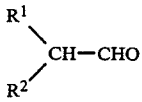

where $R^1$ and $R^2$ have the above meanings, is reacted with a carbamate of the formula

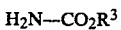

where $R^3$ is an aliphatic, cycloaliphatic or araliphatic radical, to give an N-(1-alkenyl)-carbamate of the formula

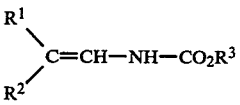

where $R^1$, $R^2$ and $R^3$ have the above meanings, and the compound IV is heated at from 250° to 600° C.

If 2-phenyl-propanol and methyl carbamate are used, the reaction can be represented by the following equation:

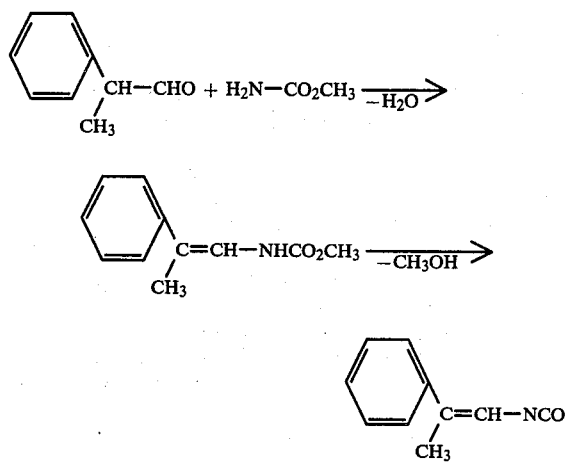

Surprisingly, compared with the prior art the process according to the invention gives 1-alkenyl isocyanates in a better yield and purity by a simpler and more economical route from starting materials which are commercially readily available and in a manner which is acceptable from the point of view of safety, that is to say, in particular, avoiding phosgene or azides in the preparation of intermediates. These advantageous properties of the process according to the invention could not have been predicted, since it is known that 1-alkenyl isocyanates are relatively unstable compounds, so that their preparation by splitting of carbamates (thermolysis) was not previously considered. The ease of splitting of the claimed O-alkyl N-(1-alkenyl)-carbamates is surprising, in view of the teaching in German Laid-Open Application DOS No. 2,756,928, page 5, that aryl carbamates are split under milder conditions than alkyl carbamates.

Preferred starting substances II and III, preferred compounds IV and hence preferred end products I are those where $R^1$, $R^2$ and $R^3$ can be identical or different and each is alkyl of 1 to 12, in particular 1 to 8, carbon atoms, cyclohexyl, or aralkyl of 7 to 12 carbon atoms, or $R^1$ and $R^2$ are each alkylaryl of 7 to 12 carbon atoms, phenyl, hydrogen, bromine or, in particular, chlorine, or $R^1$ and $R^2$, together with the adjacent carbon atom, form a 5-membered or 6-membered alicyclic ring. The above radicals can also be substituted by groups which are inert under the reaction conditions, for example alkyl or alkoxy each of 1 to 4 carbon atoms.

Examples of suitable starting substances II are: acetaldehyde, propionaldehyde, n-butyraldehyde, isobutyraldehyde, dichloroacetaldehyde, chloroacetaldehyde, α-chloropropionaldehyde, cyclohexylacetaldehyde, phenylpropionaldehyde, phenethylaldehyde, 2-methylbutyraldehyde, 2-ethylcaproaldehyde, n-valeraldehyde, isovaleraldehyde, n-caproaldehyde, isocaproaldehyde, 2-methyl-valeraldehyde, 3-methyl-valeraldehyde, 2-ethylbutyraldehyde, 2,3-dimethylbutyraldehyde, 3,3-dimethylbutyraldehyde, enanthaldehyde, 2-methyl-caproaldehyde, 3-methyl-caproaldehyde, 4-methylcaproaldehyde, 5-methyl-caproaldehyde, 2-ethyl-valeraldehyde, 3-ethyl-valeraldehyde, 3,3-dimethylvaleraldehyde, 2,3-dimethylvaleraldehyde, 4-ethylvaleraldehyde, 4,4-dimethylvaleraldehyde, 3,4-dimethylvaleraldehyde, 2,4-dimethylvaleraldehyde, 2-ethyl-2-methyl-butyraldehyde and 2-ethyl-3-methyl-butyraldehyde. Preferred compounds are: acetaldehyde, n-propanol, n-butanal, i-butyraldehyde, n-pentanal, 2-methyl-butanal, 2-methyl-pentanal, 2-phenyl-propanal, 2-ethylhexanal, 2,3-dimethyl-butanal and cyclohexylacetaldehyde.

Examples of suitable starting substances III are: octyl carbamate, nonyl carbamate, decyl carbamate, ethyl carbamate, propyl carbamate, isopropyl carbamate, butyl carbamate, undecyl carbamate, dodecyl carbamate, isobutyl carbamate, sec.-butyl carbamate, pentyl carbamate, 3-methyl-butyl carbamate, hexyl carbamate, 2-ethylhexyl carbamate, cyclohexyl carbamate, cyclopentyl carbamate, benzyl carbamate, methyl carbamate and heptyl carbamate.

In contrast to aromatic carbamates (Chem. Rev. 65 (1965), 570), the unsubstituted aliphatic carbamates of the formula III are accessible in a simple manner from urea and a corresponding alcohol, without using phosgene. Methyl carbamate, ethyl carbamate, n-butyl carbamate, n-octyl carbamate and benzyl carbamate are preferred.

The reaction in the 1st step, that is to say the preparation of the starting compound IV, is advantageously carried out at from $-20°$ to $+150°$ C., preferably from $0°$ to $100°$ C. and especially from $10°$ to $60°$ C., under atmospheric or superatmospheric pressure, batchwise or continuously. It is advantageous to use solvents which are inert under the reaction conditions, but the reaction can also be carried out without a solvent. Examples of solvents which can be used are: aromatic hydrocarbons, eg. toluene, ethylbenzene, o-, m- and p-xylene and isopropylbenzene; halohydrocarbons, especially chlorohydrocarbons, eg. tetrachloroethylene, 1,1,2,2- and 1,1,1,2-tetrachloroethane, amyl chloride, dichloropropane, methylene chloride, dichlorobutane, chloroform, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, chlorobenzene, o-, p- and m-dichlorobenzene, o-, m- and p-chlorotoluene and 1,2,4-trichlorobenzene; ethers, eg. ethyl propyl ether, n-butyl ethyl ether, din-butyl ether, diisobutyl ether, diisoamyl ether, diisopropyl ether, cyclohexyl methyl ether, diethyl ether, ethylene glycol dimethyl ether, tetrahydrofuran and dioxane; alkanols and cycloalkanols, eg. ethanol, methanol, n-butanol, isobutanol, n-propanol, isopropanol, amyl alcohol, cyclohexanol, 2-methyl-pentan-4-ol, ethylene glycol monoethyl ether, 2-ethylhexanol, methylglycol, n-hexanol, isohexyl alcohol, isoheptyl alcohol, n-heptanol, ethylbutanol, nonyl alcohol and methylcyclohexanol, and especially alcohols of 1 to 8 carbon atoms; aliphatic or cycloaliphatic hydrocarbons, eg. heptane, nonane, gasoline fractions with a boiling range of from $70°$ to $190°$ C., cyclohexane, methylcyclohexane, decalin, petroleum ether, hexane, naphtha, 2,2,4-trimethylpentane, 2,2,3-trimethylpentane, 2,3,3-trimethylpentane and octane; and mixtures of these. From 50 to 10,000 percent by weight, preferably from 100 to 500 percent by weight, based on the starting material II, of the solvent is advantageously used.

The reaction is advantageously carried out in the presence of from 0.0001 to 0.1, in particular from 0.001 to 0.05, equivalent of an acid, as a catalyst, per mole of starting material II. Inorganic or organic acids can be used. Instead of monobasic acids, equivalent amounts of polybasic acids can also be used. Examples of suitable acids are: hydrogen chloride, hydrogen bromide, perchloric acid, sulfuric acid, phosphoric acid and nitric acid; sulfonic acids, such as benzenesulfonic acid and p-toluenesulfonic acid; boron-containing acids, such as boric acid and hydrofluoboric acid; aliphatic carboxylic acids, such as chloroacetic acid, dichloroacetic acid, trichloroacetic acid, oxalic acid, formic acid, cyanoacetic acid, acetic acid, propionic acid, butyric acid, isobutyric acid, glycolic acid, lactic acid, pyruvic acid, tartaric acid, citric acid, $\alpha$- and $\beta$-chloropropionic acid, succinic acid, isovaleric acid, valeric acid, glutaric acid, adipic acid and maleic acid; benzoic acid, 2,3-, 2,4-, 2,5- and 2,6-dimethylbenzoic acid, o-, m- and p-hydroxybenzoic acid, phenylpropionic acid and cyclohexanecarboxylic acid; and appropriate mixtures. The acids can be used in concentrated form and as mixtures with one another and/or with a solvent, in particular water. Hydrochloric acid, sulfuric acid, phosphoric acid, p-toluenesulfonic acid, monochloroacetic acid, dichloroacetic acid and trichloroacetic acid are preferred.

The reaction can be carried out as follows: a mixture of solvent, acid and starting materials II and III is kept at the reaction temperature for from 0.5 to 25 hours and is then fractionally distilled. The compound IV can be isolated or can be introduced directly into the reactor for the 2nd step of the preparation of isocyanates.

The reaction in the 2nd step, that is to say the splitting, is effected by heating the compound IV to a temperature within the above range. The end product I is then separated out of the mixture in a conventional manner, for example by fractional distillation. The splitting reaction is advantageously carried out by introducing the N-(1-alkenyl)-carbamate IV directly into the reactor, or first vaporizing it in a vaporizer zone upstream of the pyrolysis reactor and then passing the vapors through the reactor. The vapors issuing from the reactor are passed to a separating device which allows the end product I formed to be separated off from the alcohol $R^3OH$, in order to avoid recombination. An example of a suitable separating device is a fractional condensation apparatus. Another useful embodiment is, for example, fractional distillation over a column, in which case an inert solvent can be used as an intermediate-boiler. If necessary, the end product can then be purified, for example by distillation or crystallization, or separated off from any unreacted starting material. A suitable pyrolysis reactor is an apparatus in which the carbamates or their vapors can be brought to the desired temperature extremely rapidly, for example a heated tube filled with packing which serves as a heat transfer medium, or a fluidized bed.

The splitting is carried out at from $250°$ to $600°$ C., preferably from $350°$ to $550°$ C., especially from $400°$ to $550°$ C. and advantageously from $400°$ to $500°$ C., under atmospheric, superatmospheric or reduced pressure, preferably under from 0.1 to 1,033 mbar, especially from 0.5 to 500 mbar and advantageously from 1 to 200 mbar, and continuously or batchwise, as expedient. It can be carried out with the addition of inert gases, for example nitrogen, or in the presence of inert solvents, in particular those solvents which have a boiling point between that of the end product I and that of the alcohol component $R^3OH$ (intermediate-boiler). The throughput is advantageously from 0.05 to 0.5 kg of carbamate IV per liter and hour, and depends on the splitting temperature chosen and the desired conversion. Unreacted starting material is recycled.

The splitting reaction can also be carried out in the liquid phase under superatmospheric, atmospheric or reduced pressure, in which case, for example, the carbamate IV is introduced, with stirring, into a reactor containing a high-boiling inert solvent as a heat transfer medium, for example an oil of boiling point 300°–400° C. The vapors issuing from the reactor are separated and worked up as in the splitting process described above. The liquid phase splitting is preferably carried out at from 250° to 400° C.

Examples of suitable N-(1-alkenyl)-carbamates IV are all those prepared from the starting materials II and III listed as being suitable, such as methyl N-vinylcarbamate, ethyl N-vinylcarbamate, ethyl N-(1-propenyl)-carbamate, ethyl N-(1-butenyl)-carbamate, ethyl N-(2-methyl-1-propenyl)-carbamate and ethyl N-(2-methyl-1-butenyl)-carbamate. Particularly suitable N-(1-alkenyl)-carbamates are those which give an end product I and an alcohol with a difference in boiling points sufficient to permit simple separation, for example n-butyl N-vinyl carbamate, methyl N-(1-pentenyl)-carbamate, n-octyl N-(2-methyl-1-propenyl)-carbamate, ethyl N-(2-methyl-1-pentenyl)-carbamate and methyl N-(2-phenyl-1-propenyl)-carbamate.

The 1,2-unsaturated isocyanates I which can be prepared according to the invention are valuable starting materials for the preparation of pest control agents, dyes, drugs, textile water-repellents, detergents, plastics, bleaches and adhesives, since they possess an activated double bond or an activated α-carbon atom in addition to a reactive isocyanate group. Furthermore, 1-alkenyl isocyanates are important monomers which can be reacted in many ways to give chain polymers and ladder polymers, for example radiation-curing surface-coating resins (Chem. High Polymers (Tokyo) 13 (1956), 390; J. Polym. Sci. 35 (1959), 215; J. Org. Chem. 26 (1961), 770; and J. Coatings Techn. 49 (1977), 82. They can be reacted to give urethanes, for example for use as foams or high molecular weight coatings with a high degree of flexibility, or ureas. Concerning uses, reference may be made to the above publications and to Ullmanns Encyklopädie der technischen Chemie, Volume 9, pages 11, 12 and 404 and Volume 17, page 204 (3rd edition).

In the Examples which follow, parts are by weight and bear the same relation to parts by volume as the kilogram to the liter.

EXAMPLE 1

(a) 402 parts of 2-phenylpropanal and 5 parts of p-toluenesulfonic acid are added in succession to a solution of 450 parts of methyl carbamate in 1,500 parts by volume of diethyl ether at 25° C., with stirring. After a reaction time of 45 minutes, fractional distillation of the solid obtained gives 468.6 parts (81.8% of theory, based on 2-phenylpropanal employed) of methyl N-(2-phenyl-1-propenyl)-carbamate as a cis/trans isomer mixture of boiling point 131°–136° C./0.4 mbar, and 214.3 parts of methyl carbamate, which can be re-used.

(b) The methyl N-(2-phenyl-1-propenyl)-carbamate obtained in Example 1(a) is vaporized continuously at 200° C./4 mbar in a vaporizer consisting of an electrically heated quartz tube, and the vapors are passed, at 500° C./4 mbar, through an electrically heated quartz tube packed with 250 parts by volume of V$_2$A wire mesh rings (φ3 mm). 2-Phenyl-1-propenyl isocyanate and unreacted compound IV are first condensed, at about 10° C. (water cooling), out of the vapors issuing from the tube, whilst the methanol formed condenses at −78° C. in a subsequent dry ice cold trap. After a total reaction time of 15 hours, fractional distillation of the condensate gives 83.9 parts of compound IV (82.1% conversion) and 273.5 parts of 2-phenyl-1-propenyl isocyanate (70.1% yield, based on methyl N-(2-phenyl-1-propenyl)-carbamate employed, or 85.3% yield, based on methyl N-(2-phenyl-1-propenyl)-carbamate reacted) as a cis/trans isomer mixture of boiling point 62°–67° C./0.5 mbar.

EXAMPLE 2

(a) 126 parts of isobutyraldehyde and 7 parts of p-toluenesulfonic acid are added in succession to a solution of 605.5 parts of n-octyl carbamate in 1,750 parts by volume of diethyl ether at 25° C., after which the temperature rises to 40° C. for one hour. After one day, the solid product which as crystallized out is filtered off with suction and fractionally distilled in the presence of 10 parts of p-toluenesulfonic acid and one part of hydroquinone. 298.3 parts of n-octyl N-(2-methyl-1-propenyl)-carbamate (75.1% yield, based on isobutyraldehyde employed) of boiling point 126° C./1 mbar are obtained, and 279.5 parts of n-octyl carbamate are recovered and can be re-used.

(b) The n-octyl N-(2-methyl-1-propenyl)-carbamate obtained in Example 2(a) is continuously vaporized at 200° C./2.7 mbar in a vaporizer consisting of an electrically heated quartz tube, and the vapors are passed, at 450° C./2.7 mbar, through an electrically heated quartz tube packed with 220 parts by volume of V$_2$A wire mesh rings (φ3 mm). Octanol and unreacted compound IV are first condensed, at about 10° C. (water cooling), out of the vapors issuing from the tube, whilst the 2-methyl-1-propenyl isocyanate formed is condensed at −78° C. in a subsequent dry ice cold trap. After a total reaction time of 14 hours, fractional distillation gives 90.1 parts of compound IV (69.8% conversion) and 83 parts of 2-methyl-1-propenyl isocyanate (65.1% yield, based on n-octyl N-(2-methyl-1-propenyl)-carbamate employed, or 93.3% yield, based on n-octyl N-(2-methyl-1-propenyl)-carbamate reacted) of boiling point 58° C./200 mbar.

EXAMPLE 3

(a) 430 parts of n-valeraldehyde and 5 parts of p-toluenesulfonic acid are added in succession to a solution of 750 parts of methyl carbamate in 2,000 parts by volume of diethyl ether at 25° C. After a reaction time of one hour, in which the temperature rises to 40° C., filtration with suction and subsequent fractional distillation of the solid in the presence of 15 parts of potassium carbonate and 2 parts of hydroquinone give 559.1 parts of methyl N-(1-pentenyl)-carbamate (78.2% yield, based on n-valeraldehyde employed) as a cis/trans isomer mixture of boiling point 97°–102° C./16 mbar, and 352.5 parts of methyl carbamate, which can be re-used.

(b) The methyl N-(1-pentenyl)-carbamate obtained in Example 3(a) is vaporized continuously at 160°–170° C./80 mbar in a vaporizer consisting of an electrically heated quartz tube, and the vapors are passed, at 450° C./80 mbar, through an electrically heated quartz tube packed with 140 parts by volume of V$_2$A wire mesh rings (φ3 mm). 1-Pentenyl isocyanate and unreacted compound IV are first condensed, at about 10° C. (water cooling), out of the vapors issuing from the tube, whilst the methanol formed is condensed at −78° C. in a downstream dry ice cold trap. After a total reaction time of 23 hours, fractional distillation of the condensate gives 221.4 parts of compound IV (60.4% conversion) and 188.8 parts of 1-pentenyl isocyanate (43.5% yield, based on methyl N-(1-pentenyl)-carbamate employed, or 70% yield, based on methyl N-(1-pentenyl)-carbamate reacted) of boiling point 52°–55° C./60 mbar.

We claim:

1. A process for the preparation of a 1-alkenyl isocyanate of the formula

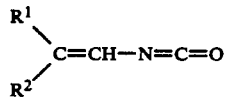  I where $R^1$ and $R^2$ can be identical or different and each is hydrogen, halogen or an aliphatic, cycloaliphatic, araliphatic or aromatic radical, or $R^1$ and $R^2$, together with the adjacent carbon, form a 5-membered or 6-membered alicyclic ring, wherein an aldehyde of the formula

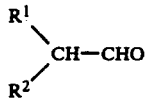  II where $R^1$ and $R^2$ have the above meanings, is reacted with a carbamate of the formula

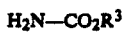  III where $R^3$ is an aliphatic, cycloaliphatic or araliphatic radical, to give an N-(1-alkenyl)-carbamate of the formula

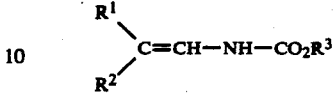  IV where $R^1$, $R^2$ and $R^3$ have the above meanings, and thereafter heating the compound IV at a temperature of from 250° to 600° C. to form compound I.

2. The process of claim 1, wherein the reaction in the 1st step is carried out at from −20° to +150° C.

3. The process of claim 1, wherein the reaction in the 1st step is carried out at from 0° to 100° C.

4. The process of claim 1, wherein the reaction is carried out using solvents which are inert under the reaction conditions.

5. The process of claim 1, wherein the reaction in the 1st step is carried out using from 0.0001 to 0.1 equivalent of acid per mole of starting material II.

6. The process of claim 1, wherein the reaction in the 2nd step is carried out at from 350° to 550° C.

7. The process of claim 1, wherein the reaction in the 2nd step is carried out at from 400° to 550° C.

8. The process of claim 1, wherein the reaction in the 2nd step is carried out under a pressure of from 0.1 to 1,033 mbar.

* * * * *